United States Patent [19]

Turner et al.

[11] Patent Number: 5,103,032

[45] Date of Patent: Apr. 7, 1992

[54] INHIBITED ACRYLOXYSILANES AND METHACRYLOXYSILANES

[75] Inventors: Scot M. Turner; George M. Omietanski, both of Marietta, Ohio

[73] Assignee: Union Carbide Chemicals & Plastics Technology Corporation, Danbury, Conn.

[21] Appl. No.: 722,175

[22] Filed: Jun. 27, 1991

[51] Int. Cl.$^5$ ................................................ C07F 7/08
[52] U.S. Cl. .................................... 556/401; 556/438; 556/442; 203/8
[58] Field of Search ................. 556/401, 438, 442; 203/8

[56] References Cited

U.S. PATENT DOCUMENTS

| | | | |
|---|---|---|---|
| 3,072,603 | 1/1963 | Tholstrup | 260/45.85 |
| 3,258,477 | 6/1966 | Plueddemann et al. | 260/48 |
| 3,526,673 | 9/1970 | Albert | 260/666.5 |
| 3,555,116 | 1/1971 | Stahly et al. | 260/864 |
| 3,816,267 | 6/1974 | Chuang | 556/401 X |
| 4,276,426 | 6/1981 | Lindner et al. | 556/479 |
| 4,709,067 | 11/1987 | Chu et al. | 556/440 |
| 4,722,807 | 2/1988 | Iwahara et al. | 556/401 X |
| 4,780,555 | 10/1988 | Bank | 556/401 X |
| 4,798,889 | 1/1989 | Plueddemann et al. | 556/401 |
| 4,927,948 | 5/1990 | Bernhardt et al. | 556/401 |

FOREIGN PATENT DOCUMENTS

| | | |
|---|---|---|
| 2145588 | 11/1984 | European Pat. Off. . |
| 3832621 | 9/1989 | Fed. Rep. of Germany ...... 556/401 |
| 1084368 | 9/1967 | United Kingdom . |

OTHER PUBLICATIONS

Baum and Perun, Antioxidant Efficiency Versus Structure, SPE Transactions, pp. 250–257 (1962).
Cas Computer Search of 2,6-Di-Tert-Butyl-Alpha-Dimethylamino-P-Cresol: 618,399 8/78 USSR, 1,098,200 5/86 USSR, RO 90563 11/86 USSR.

Primary Examiner—Paul F. Shaver
Attorney, Agent, or Firm—J. F. Leightner

[57] ABSTRACT

Compositions containing an acryloxysilane or a methacryloxysilane and an N,N-dialkylaminomethylene phenol in an amount at least sufficient to inhibit polymerization of the silane during its formation, purification and storage. Methods for producing such compositions are also provided.

25 Claims, No Drawings

INHIBITED ACRYLOXYSILANES AND METHACRYLOXYSILANES

FIELD OF INVENTION

This invention relates to acryloxysilanes and methacryloxysilanes having enhanced stability towards polymerization prior to end use application. This invention also relates to stabilization of such compounds during their initial formation, purification and storage.

BACKGROUND OF THE INVENTION

Acryloxysilanes and methacryloxysilanes are chemically reactive materials which are useful in many commercial applications. For example, such compounds are useful as coupling agents to bond organic compounds to inorganic materials. In particular, 3-methacryloxypropyltrimethoxysilane is widely used as a coupling agent in enhancing the performance of fiberglass-reinforced products.

Acryloxysilanes and methacryloxysilanes can be prepared by the known reaction between organosilicon compounds having an Si—H functional group and acryloxy and methacryloxy compounds having additional aliphatic unsaturation. For example, 3-methacryloxypropyltrimethoxysilane (sometimes herein referred to for brevity as "MAOP-TMS") can be prepared by the known reaction of allyl methacrylate with trimethoxysilane, as shown by the following equation (1):

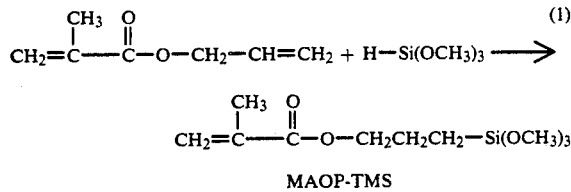

Likewise, reaction of allyl methacrylate with trichlorosilane, H—SiCl$_3$, provides 3-methacryloxypropyltrichlorosilane which in turn can be reacted with methanol to produce MAOP-TMS. When allyl acrylate is used in place of allyl methacrylate, the corresponding acryloxypropyltrimethoxy- (or trichloro-) silanes are provided. Due to the exothermic nature of such hydrosilation reactions, polymerization of the highly reactive acryloxysilane and methacryloxysilane product can occur as product is formed. Such polymerization can also be induced during esterification of the trichlorosilane intermediate to the corresponding trialkoxysilane product, such as, for example, during the aforementioned reaction of 3-methacryloxypropyltrichlorosilane with methanol to produce MAOP-TMS.

Undesired polymerization can also occur during purification of the crude reaction product. Typically, purification is accomplished by distillation, which is preferably carried out at as low a temperature as feasible to minimize polymerization. Even purified product may tend to polymerize during storage prior to end use.

Depending on the extent of such polymerization during initial formation, purification and storage of acryloxy- and methacryloxysilanes, thickening and even gelling may occur, resulting in increased maintenance to remove the thickened or gelled material from equipment or in unsalable product.

Various approaches are known to the art for minimizing undesired polymerization of acryloxy- and methacryloxysilanes during their manufacture. One such approach, described in U.S. Pat. No. 4,276,426 to Lindner et al., comprises continuously charging the reactants to a pipe-shaped reactor, and continuously circulating the reaction mixture at a velocity of at least 1000 centimeters per minute. In one embodiment of this patent, allyl methacrylate, trichlorosilane and a platinum catalyst are continuously circulated at a velocity of 3500 centimeters per minute. The patentees report that when the same reaction is repeated without circulation, "the contents of the reactor jelled" after one hour (column 5, lines 13-16). It is evident that this technique for avoiding polymerization during the hydrosilation reaction requires high speed continuous operation and is susceptible to gelling as a result of process fluctuation.

Another approach to producing stable acryloxy- and methacryloxysilanes is to employ polymerization inhibitors such as those disclosed in: U.S. Pat. No. 3,258,477 to Plueddemann et al.; U.S. Pat. No. 4,709,067 to Chu et al.; and U.S. Pat. No. 3,816,267 to Chuang.

The Plueddemann et al. patent describes a variety of reactions for preparing acryloxy- and methacryloxysilanes including hydrosilation, illustrated by above equation (1). In effecting such reactions, Plueddemann et al. state the desirability of using "polymerization inhibitors such as copper acetate and hydroquinone to prevent polymerization of the silane product by way of the acrylate double bond" (column 3, lines 66-69). In illustrating the formation of 3-acryloxy- and 3-methacryloxypropylsilanes by the platinum-catalyzed hydrosilation of allyl acrylate and allyl methacrylate with trimethoxy- or tricholorosilane, Plueddemann et al. employ 2,5-ditertiary butyl hydroquinone (Examples 1 and 2) and hydroquinone (Example 9) as polymerization inhibitors at levels exceeding 1000 parts by weight per million parts by weight (ppm) of silane product. Another reaction described by Plueddemann et al. for producing acryloxy- and methacryloxysilanes comprises the platinum-catalyzed reaction of a tertiary-amine salt of acrylic or methacrylic acid with a chloroalkylsilane. In effecting this type of reaction, Plueddemann et al. state: "It is also best to carry out the reaction in the presence of one or more polymerization inhibitors for acrylic or methacrylic acid, such as hydroquinone and N,N'-diphenylphenylene diamine" (column 4, lines 16-19). In illustrating this particular reaction using triethylamine, methacrylic acid and chloromethyltrimethoxysilane Plueddemann et al. employ in their Example 5, hydroquinone as the inhibitor, again at a high level of at least 1000 ppm of the methacryloxytrimethoxysilane product.

Further, U.S. Pat. No. 4,709,067 to Chu et al. discloses a multi-step process for preparing acryloxy- and methacryloxysilanes. The first three steps involve: charging an inhibited acryloxy or methacryloxy functional compound to a first reservoir; charging an Si—H compound and platinum catalyst to a second reservoir; and combining the contents of the two reservoirs in a reactor in which the hydrosilation is effected. In addition to the presence of inhibitor during the hydrosilation reaction, additional inhibitor is added to the crude reaction product prior to vacuum distillation.

More specifically, Chu et al. employ phenolic inhibitors such as the monomethyl ether of hydroquinone, Ionol TM and Isonox TM 129; aromatic amines such as diphenylene diamine; and aromatic sulfur compounds such as phenothiazine. (Ionol® is 2,6-di-tert-butyl-4- methyl phenol; ACS SOCMA Handbook, p. 63A, 1965. Isonox ™ 129 is 2,2'-ethylidenebis[4,6-di-tert-butylphenol]; ACS On-Line File Registry of Chemical Trademarks, RN 35958-30-6, 1991). In the preferred embodiment of Chu et al., only the phenolic inhibitors are used in the hydrosilation reaction step and a combination of both phenolic and non-phenolic inhibitors is used during vacuum distillation. The concentration of inhibitor used during hydrosilation varies from 0.2 to 5.0% by weight (2,000 to 50,000 ppm) of the silylated acrylate or methacrylate product. During vacuum distillation the concentration of the non phenolic inhibitor varies from 200 to 10,000 ppm, while the concentration of phenolic inhibitor varies from 500 to 15,000 ppm, based on the weight of methacryloxysilane product distilled.

The aforementioned U.S. Pat. No. 3,816,267 to Chuang relates to the distillation of acrylates and methacrylates in the presence of certain polymerization inhibitors. Chuang employs as inhibitors a mixture of a quinone and an enol derivative of a quinone in an amount sufficient to prevent polymerization. Preferably, at least 100 ppm of each inhibitor is used during the distillation process. Lower inhibitor levels (i.e. 10 ppm) can be utilized " . . . if the temperature within the column is low, and one employs reduced pressure, and the distillation is not prolonged . . . " (Column 3, lines 52-57).

In addition to stabilization of acrylates and methacrylates, Chuang discloses the applicability of his polymerization inhibitors to acryloxy- and methacryloxysilanes. For example, at column 4, lines 46-44, Chuang states:

" . . . the methacrylate and acrylate esters which have a hydrolyzable silicon group bonded to the ester moiety, such as a trimethoxysilyl moiety, represent the most difficult to stabilize from distillation when distilled from a crude mixture containing them. The basis for this is the belief that during distillation, heat causes a certain number of the hydrolyzable groups, such as, for example, methoxy groups, to be cleaved from the silicon atom and act as a free radical which induces polymerization at a lower temperature than would be normally expected for such an acrylate or methacrylate molecule. Hence, a severe test for inhibiting the polymerization of acrylate and methacrylate esters would be the stabilization of such methacrylato or acrylato silane esters . . . . "

In illustrating the applicability of his dual inhibitor system to 3-methacryloxypropyltrimethoxysilane, Chuang employs total inhibitor levels ranging from 100-700 ppm during the distillation thereof.

As is evident from the above discussion of the Plueddemann et al., Chu et al. and Chuang patents, the state of the art is such that high levels (at least 1000 ppm) of polymerization inhibitors are employed in the initial formation of acryloxy- and methacryloxysilanes and that, even during their purification by vacuum distillation, at least 100 ppm of inhibitor is used. Such levels of inhibitor can have adverse effects on product properties such as color. A color problem, for example, can be reduced by lowering the level of inhibitor used. Unfortunately, with reduced inhibitor levels the risk of undesired product polymerization increases.

A still further approach for dealing with the polymerization problem is described in U.S. Pat. No. 4,780,555 to Bank. This patent discloses a method for stabilizing acryl-functional halosilanes made by reacting a halosilane having an Si—H group with an acryloxy- or methacryloxy-functional organic compound in the presence of a platinum catalyst. The acryl-functional halosilane is inhibited with 100 to 2,000 ppm of phenothiazine while sparging the reaction mixture with a gas composition containing at least 0.1%, preferably from 2 to 4%, by volume oxygen in an inert gas such as nitrogen. A drawback of this method is that the disclosed inhibitor system is effective only when the specified oxygen level is present.

Accordingly, a need exists to stabilize acryloxy- and methacryloxysilanes against polymerization with an inhibitor which is capable of inhibiting polymerization at low concentrations and which is effective under aerobic as well as non-aerobic conditions and does not require special process features to be effective. It also is desirable that such an inhibitor not cause discoloration of the inhibited product, even when the inhibitor is used in relatively high concentrations.

SUMMARY OF THE INVENTION

The present invention provides acryloxysilane and methacryloxysilane compositions stabilized with N,N-dialkylaminomethylene phenols. Such phenolic compounds are capable of inhibiting polymerization of acryloxy- and methacryloxysilanes at very low levels, and are effective in both the presence and absence of molecular oxygen. The present invention also provides a method for stabilizing acryloxy- and methacryloxysilanes which comprises providing to such silanes an N,N-dialkylaminomethylene phenol in an amount at least sufficient to inhibit polymerization of the silane. The N,N-dialkylaminomethylene phenol can be provided to the reaction mixture used to form the desired acryloxy- or methacryloxysilane, to the crude reaction product during purification, and to the final product to prolong shelf life.

It is to be understood that the generic expression "(meth)acryloxy" as sometimes used herein for brevity includes the acryloxy moiety, $CH_2=CH-C(O)O-$, and the methacryloxy moiety, $CH_2=C(CH_3)-C(O)O-$.

DETAILED DESCRIPTION OF THE INVENTION

The phenolic inhibitors employed in accordance with the teachings of this invention have, as an essential substituent, an N,N-dialkylaminomethylene group having the formula, $(R^1)(R^2)N-CH_2-$, where $R^1$ and $R^2$ are alkyl. In addition to the essential phenolic hydroxyl and tertiary-aminomethylene substituents, the benzene nucleus may be further substituted with one or two alkyl groups, $R^3$ and $R^4$, as shown by the formula:

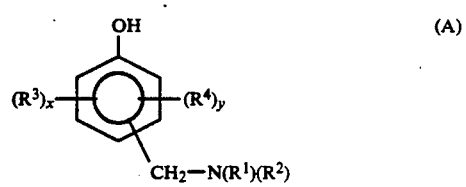

where x and y are zero or one, and the sum x+y is zero, one or two. It is to be understood that the alkyl groups, $R^1$, $R^2$, $R^3$ and $R^4$, can be the same as or different from one another.

Preferably, the N,N-dialkylaminomethylene group is positioned ortho or para to the phenolic hydroxyl and, when present, the alkyls bonded directly to the benzene nucleus are positioned meta to the N,N-dialkylaminomethylene group. Thus, preferred classes of the inhibitors are:
2-N,N-dialkylaminomethylene phenols;
4-N,N-dialkylaminomethylene phenols;
2-alkyl-4-N,N-dialkylaminomethylene phenols;
4-alkyl-2-N,N-dialkylaminomethylene phenols;
2,6-dialkyl-4-N,N-dialkylaminomethylene phenols; and
2,4-dialkyl-6-N,N-dialkylaminomethylene phenols.

The alkyl ($R^1$ and $R^2$) groups of the N,N-dialkylaminomethylene substituent, as well as, when present, the alkyl substituents ($R^3$ and $R^4$) bonded directly to the benzene nucleus, have from one to 18 carbon atoms and may be linear or branched. Illustrative of suitable alkyls ($R^1$-$R^4$) are: methyl, ethyl, propyl, isopropyl, butyl, isobutyl, tertiary-butyl, tertiary-pentyl, hexyl, octyl, decyl, dodecyl, hexadecyl, and octadecyl. Usually, the alkyl groups have from one to four carbon atoms.

The particularly preferred classes of compounds for use as polymerization inhibitors as described herein are the 2,6-dialkyl-4-N,N-dialkylaminomethylene phenols, and 2,4-dialkyl-6-N,N-dialkylaminomethylene phenols, encompassed by the following respective formulas:

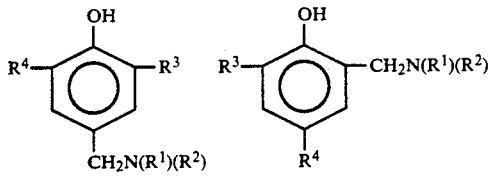

where $R^1$-$R^4$ are as above-defined, and preferably have from one to four carbon atoms.

The inhibitors employed in accordance with this invention are known compounds. They are readily obtainable by the well-known Mannich reaction involving the reaction of phenol or an alkyl-substituted phenol with a secondary amine and formaldehyde. See, for example, T. H. Coffield et al., *J. Am. Chem. Soc.* 79, 5019-5023 (1957).

Illustrative of specific N,N-dialkylaminomethylene phenols useful in this invention are:
2-tert-butyl-4-dimethylaminomethylene phenol,
4-isopropyl-2-dimethylaminomethylene phenol,
2-isopropyl-4-dimethylaminomethylene phenol,
2,6-dimethyl-4-dimethylaminomethylene phenol,
2-methyl-6-tert-butyl-4-dimethylaminomethylene phenol,
2,6-dimethyl-4-dibutylaminomethylene phenol,
2,6-diisopropyl-4-dimethylaminomethylene phenol,
2,6-di-tert-butyl-4-N-methyl-N-ethylaminomethylene phenol,
2,6-di-tert-butyl-4-dimethylaminomethylene phenol,
2-methyl-6-tert-butyl-4-diamylaminomethylene phenol,
2,6-diisopropyl-4-diethylaminomethylene phenol,
and 2,6-di-tert-butyl-4-dipropylaminomethylene phenol.

Especially preferred is
2,6-di-tert-butyl-4-dimethylaminomethylene phenol.
This material is commercially available under the tradename ETHANOX® 703.

In the (meth)acryloxysilanes which are stabilized with the above-described N,N-dialkylaminomethylene phenol inhibitors, the (meth)acryloxy moieties are bonded to silicon through an alkylene or alkyleneoxy bridge and silicon is further bonded to alkoxy groups or halide. More particularly, suitable silanes are those encompassed by the general formula:

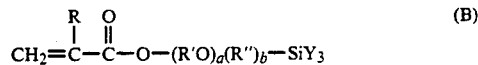

where:
R is hydrogen or methyl;
R' is alkylene of two to four carbon atoms;
R" is alkylene of one to four carbon atoms;
Y is halide, alkoxy or alkoxy-substituted alkoxy groups where alkoxy has one to four carbon atoms;
a is zero up to 10, and is usually no more than five;
b is zero or 1; and
a+b is at least one up to 11, and is usually no more than six.

The R' and R" groups may be linear or branched, and any combination of such groups can be present. The divalent R' group is exemplified by ethylene (—$CH_2CH_2$—) and higher homologous groups such as propylene, isopropylene and butylene. R" can be any such alkylene groups and, in addition, can be methylene. The Si-bonded Y groups can be any $C_1$-$C_4$ linear or branched alkoxy group (e.g., methoxy, ethoxy, isopropoxy) or $C_1$-$C_4$ alkoxy-substituted $C_1$-$C_4$ alkoxy groups (e.g., beta-methoxyethoxy) or any of the halides such as, in particular, chlorine and bromine.

Illustrative of such (meth)acryloxysilanes which are stabilized as described herein are:
3-acryloxypropyltrimethoxysilane,
3-acryloxypropyltriethoxysilane,
3-methacryloxypropyltrimethoxysilane,
3-methacryloxyisobutyltrimethoxysilane,
3-methacryloxypropyltriethoxysilane,
3-acryloxypropyltrichlorosilane,
3-methacryloxypropyltrichlorosilane,
3-methacryloxyisobutyltrichlorosilane,
3-methacryloxypropyl[tris(beta-methoxyethoxy)] silane, and the like.

The above-described (meth)acryloxysilanes are prepared by methods known to the art such as those described in the aforementioned U.S. Pat. No. 3,258,477 to Plueddemann et al. and U.S. Pat. No. 4,709,067 to Chu et al. For example, (meth)acryloxysilanes encompassed by Formula B above can be prepared by the reaction of an Si—H functional compound and an ester of acrylic or methacrylic acid wherein the ester moiety has an ethylenically unsaturated group, as shown by the following equation (2):

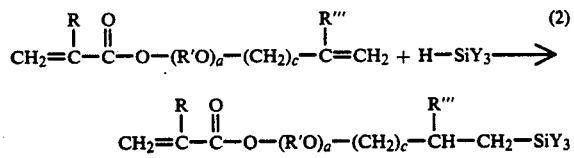

where: R, R', a and Y are as defined above with respect to Formula B; R''' is hydrogen or methyl; and c is zero or one; and the —$(CH_2)_c$—$CH(R''')CH_2$— group is illustrative of the R" alkylene group of Formula B. The hydrosilation reactions encompassed by equation (2), as well as the specific embodiments thereof discussed with reference to equation (1) above, are normally effected at a temperature from about 70° to about 120° C. in the presence of a platinum-containing catalyst. Suitable catalysts include chloroplatinic acid and those described in U.S. Pat. No. 4,709,067, beginning with column 4, line 55 through column 5, line 3.

With reference to the hydrosilation reaction of equation (2), it is to be understood that when the desired product is a (meth)acryloxytrialkoxysilane (i.e., when Y of Formula B is an alkoxy group), the Y group of the H—SiY$_3$ reactant of equation (2) can be halogen, such as in particular chlorine, or alkoxy. When Y of the reactant is chlorine, for example, the product of equation (2) is the corresponding trichlorosilane which can then be esterified with an alcohol, such as methanol, by methods known to the art to provide the desired trialkoxysilane. Alternatively, the desired trialkoxysilane can be produced directly by the hydrosilation reaction of equation (2) by the use of a trialkoxysilane reactant, H—SiY$_3$, in which Y is alkoxy. It is to be understood, therefore, that the N,N-dialkylaminomethylene phenol inhibitor used in the present invention, can be provided to the reaction mixture which produces the desired product directly, or to an intermediate reaction mixture.

In addition to hydrosilation, the (meth)acryloxysilanes which are stabilized as described herein can be prepared by the reaction of a tertiary-amine salt of acrylic or methacrylic acid with a chloroalkylsilane as described in U.S. Pat. No. 3,258,477, beginning with column 3, line 69 through column 4, line 16.

In accordance with one embodiment of the process of the present invention, the N,N-dialkylaminomethylene phenol inhibitor is provided to the reaction mixture used to produce the (meth)acryloxysilane to be stabilized. Such (meth)acryloxysilane-forming reaction mixtures include those containing the above-described hydrosilation reactants (e.g., an ethylenically unsaturated ester of acrylic or methacrylic acid and an Si—H functional compound such as a trialkoxysilane or trihalosilane), as well as reaction mixtures containing a tertiary-amine salt or an alkali metal salt of acrylic or methacrylic acid and a chloroalkylsilane (e.g., chloromethyltrimethoxysilane and chloropropyltrimethoxysilane).

In accordance with another embodiment of the process of the invention, the N,N-dialkylaminomethylene phenol inhibitor is provided to the (meth)acryloxysilane-containing mixture to be purified by distillation.

The inhibitor may be provided to the process of this invention by adding it as a separate stream directly to the zone in which the (meth)acryloxysilane is to be either formed initially or purified. Alternatively, the inhibitor can be provided to the zone as a component of one or more of the reactant streams, or as a component of the mixture to be distilled. The inhibitor can also be provided to the recovered or final product such as prior to packaging, storage or shipping. It is preferred to add the inhibitor just prior to the process steps requiring inhibition, and it is most preferred to use multiple additions of the inhibitor during the overall manufacturing process (initial reaction, purification and recovery of product). It is to be understood that the N,N-dialkylaminomethylene phenol inhibitor may be provided to any step of batch or continuous processes for (meth)acryloxysilane manufacture, without departing from the scope of this invention.

The stabilization of (meth)acryloxysilanes is effected by employing the N,N-dialkylaminomethylene phenol inhibitor in an amount at least sufficient to prohibit polymerization. The particular minimal amount used depends largely on the severity of the conditions to which the silane is subjected during its initial formation, purification and storage. For example, generally the higher the temperature the more susceptible is the silane to polymerization. Further, the lower the free oxygen content of the atmosphere to which the silane or silane-containing medium is exposed, the greater the tendency of the silane to polymerize. Some oxygen in the vapor space above the (meth)acryloxysilane is beneficial in inhibiting polymerization. However, as the concentration of oxygen in the vapor space increases, the level of dissolved oxygen in the silane-containing medium also increases. High levels of dissolved oxygen within the (meth)acryloxysilane-containing medium can lead to peroxide formation which in turn can initiate polymerization. Generally the more severe the combination of conditions to which the silane is subjected, the higher the minimal effective inhibitor level. For example, subjecting the silane or silane-containing medium to high temperatures, and to oxygen levels which promote peroxide formation, substantially increases the minimum effective amount of inhibitor.

In addition to oxygen level and temperature, other conditions which can induce polymerization of (meth)acryloxysilanes are metal contaminants, ultraviolet light and free radical initiators. Illustrative of the latter are oxygen-derived peroxy and peroxide, as well as alkoxy, aryloxy, alkyl and aryl, free radicals.

Generally, oxygen levels of approximately 0.1–4% by volume in nitrogen are believed to be beneficial in aiding inhibitors in inhibiting polymerization; see aforementioned U.S. Pat. No. 4,780,555 to Bank. However, with increasing levels of dissolved oxygen, peroxide radicals can form to an extent sufficient to initiate polymerization despite the presence of inhibitors. In order to minimize free radical formation, oxygen levels should not exceed 4% by volume throughout the (meth)acryloxysilane-forming reaction and purification process. An unexpected advantage of the use of N,N-dialkylaminomethylene phenols as inhibitors of (meth)acryloxysilanes is that molecular oxygen is not essential to their efficacy as an inhibitor. Thus, such stabilization can be effected in the substantial absence of molecular oxygen (i.e. 10 ppm by volume or less). However, it is to be understood that stabilization in accordance with the teachings of this invention can be effected in atmospheres containing up to about 4%, and preferably no more than 3%, by volume oxygen.

Generally about 5–500 ppm (parts by weight per million parts by weight of silane) of the N,N-dialkylaminomethylene phenol is sufficient to prevent polymerization of (meth)acryloxysilanes. Normally no more than 100–200 ppm is required. It is to be understood, however, that exposure of the (meth)acryloxysilanes to severe conditions will require correspondingly higher levels of inhibitor such as up to 1,000 ppm or more. For example, high temperature distillation (160°–190° C.) or exposure to a combination of conditions which accelerate polymerization such as exposure to atmospheric conditions (21% oxygen by volume) and heat (e.g. 140° C.) will result in gelling of (meth)acryloxysilanes unless substantially higher inhibitor levels are used such as 1000–2500 ppm. Typically, 10–150 ppm of inhibitor is present during the (meth)acryloxysilane-forming reaction, with an additional 10–325 ppm of inhibitor provided during distillation. A final addition of inhibitor can be added to the final product in order to stabilize it during storage and distribution, the preferred range for this purpose being 5-25 ppm.

The particular minimum effective amount of N,N-dialkylaminomethylene phenol required to inhibit polymerization during distillation depends largely on the conditions to which the medium to be distilled is subjected. Among such conditions are the pressure under which the distillation is effected, the longevity or continuity of the distillation operation and the temperature of the distillation column. Typically, (meth)acryloxysilanes have a boiling point, at atmospheric pressure, of below 350° C. It is well known in the art that vacuum distillation techniques permit the distillation to be feasible at much lower temperatures, which minimizes the risk of polymerization. Accordingly, vacuum distillation techniques also allow for the use of significantly reduced inhibitor levels during the purification process. For example, while MAOP-TMS distills at 255° C. at atmospheric pressure, the preferred embodiment of the purification process as applied to this compound comprises vacuum distillation at a head temperature between 105°-120° C. at 5 mm Hg, and more usually at 90°-100° C. at 2 mm Hg. Correspondingly, the level of N,N-dialkylaminomethylene phenol required to inhibit polymerization of MAOP-TMS during vacuum distillation also decreases. Generally required inhibitor levels during distillation of MAOP-TMS conducted at atmospheric pressure are about 50-325 ppm, while the preferred embodiment is the use of 10-200 ppm of inhibitor during vacuum distillation.

Included within the scope of the present invention is the use of the N,N-dialkylaminomethylene phenol in combination with other polymerization inhibitors including those containing phenolic (—OH), amino (—NH) and quinone (O=C) functionality. Illustrative of such other inhibitors are: hydroquinone, benzoquinone, the monomethyl ether of hydroquinone, N,N'-diphenyl-p-phenylenediamine, phenothiazine, Ionol TM and Isonox TM 129, including mixtures thereof. The N,N-dialkylaminomethylene phenol is present in such combinations in an amount sufficient to provide a polymerization inhibitor system having improved performance relative to said other inhibitors or mixtures of said other inhibitors not containing the N,N-dialkylaminomethylene phenol.

The inhibitor is typically provided to the (meth)acryloxysilane-forming reaction and purification process as a solution. This technique provides more uniform dispersion of the inhibitor throughout the medium to be stabilized. Any solvent of N,N-dialkylaminomethylene phenols may be used provided the solvent does not adversely effect product quality or process control. Typically, the solvents selected are aromatic hydrocarbons well known in the art. These solvents include toluene, benzene and xylene, with toluene being preferred.

The extent of polymerization of (meth)acryloxysilanes can be determined by viscosity measurement. Such silanes are low viscosity materials which thicken dramatically when polymerization occurs. Unpolymerized (meth)acryloxysilanes have a viscosity of less than 5 centistokes at 25° C. The viscosity of (meth)acryloxysilanes slowly begins to rise with polymerization, until a point is reached where the viscosity rapidly increases, resulting in a highly viscous material (i.e., 1,000 centistokes), shortly before the material completely gels.

Gel time testing can be performed by several techniques known to the art including the use of viscometry to directly monitor the viscosity of a given (meth)acryloxysilane-containing medium. An alternative method is described by Chuang (U.S. Pat. No. 3,816,267, column 5, lines 29-42) in which a container for the sample to be tested is partially immersed in an oil bath maintained at a constant temperature, and is provided with a thermocouple and a magnetic stirring bar. The sample has a temperature approximately 10° C. lower than the oil bath as long as the magnetic stirrer is rotating. When the sample gels, the stirrer stops rotating and the sample temperature begins to rise. The temperature increase is detected by the thermocouple. In the method described by Chuang, gel time is defined as the time required to reach a detectable temperature rise. Another method, described in greater detail herein below with reference to the examples, depends on the temperature differential between the medium being tested and a constant temperature bath.

It has been found that the N,N-dialkylaminomethylene phenols are more effective, at least when compared on a microequivalent basis, in inhibiting polymerization of (meth)acryloxysilanes than other phenolic or non-phenolic inhibitors used in commercial practice.

A microequivalent is one millionth of a mole of the inhibitor divided by the number of polymerization inhibiting sites or functionalities contained in the molecule. The functionalities generally found in phenolic type polymerization inhibitors are —OH, N—H or =O groups. Therefore, when the molecule contains one functional group, for example one —OH group, then one microequivalent is one millionth of a mole of that molecule. When the molecule contains two functional groups, such as two —OH groups, then two microequivalents are present in a millionth of a mole of the molecule. Therefore, it is a better comparison of inhibitors to use equivalents of a compound rather than moles, especially when difunctional inhibitors are being compared to monofunctional inhibitors. To demonstrate the same efficiency, the difunctional inhibitors should be twice as potent as monofunctional inhibitors on an equal equivalents basis.

The following Table A sets forth the molecular weight and equivalent weight of the inhibitors used in the Examples. As is apparent from Table A, hydroquinone, benzoquinone and the diamine are difunctional molecules. For the structure of the listed compounds, refer to the description captioned "Definitions" hereinbelow.

TABLE A

|  | Molecular Weight | Equivalent Weight |
|---|---|---|
| Inhibitor I | 263 | 263 |
| Isonox 129 | 438 | 219 |
| Hydroquinone | 110 | 55 |
| Benzoquinone | 108 | 54 |
| MEHQ | 124 | 124 |
| Phenothiazine | 199 | 199 |
| N,N'-diphenyl-p-phenylenediamine | 260 | 130 |
| Ionol ® | 220 | 220 |

The Examples which follow are presented for the purpose of illustrating the invention and are not to be construed as unduly limiting thereon. All parts and percentages are by weight unless otherwise specified. In the Examples, the amount of inhibitor employed is expressed on a weight basis, as well as on the basis of equivalents. Since, as discussed above, equivalents take into account both functionality and molecular weight of an inhibitor, this basis is considered to provide the best comparison of inhibitor effectiveness.

GELLATION TEST

The procedure used to determine gel time in the Examples is as follows A thermocouple is used to measure the temperature of the (meth)acryloxysilane sample to be tested. The vessel containing the sample is immersed in a constant temperature oil bath. The sample is either agitated or not as described in the respective Examples, and the temperature of the oil bath and the sample is allowed to equalize. When polymerization begins to occur, the viscosity of the sample increases and a temperature gradient is detected. Eventually, with increasing polymerization, the temperature of the (meth)acryloxysilane sample will register as a temperature differential compared to the constant temperature oil bath. For purposes of the Examples, the sample was considered to have gelled when the temperature within the sample deviated by 2.0° C. from the constant oil bath temperature.

DEFINITIONS

The following designations used in the Examples and elsewhere herein have the following meaning:

Inhibitor I - 2,6-di-tert-butyl-alpha-dimethyl-
aminomethylene phenol (Ethanox ® 703)

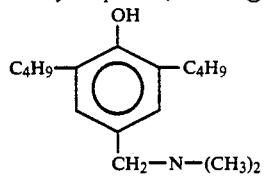

MEHQ - monomethyl ether of hydroquinone

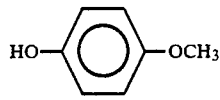

Phenothiazine

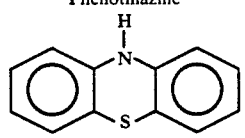

N,N'-diphenyl-p-phenylenediamine

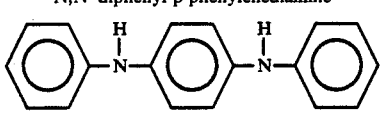

Hydroquinone

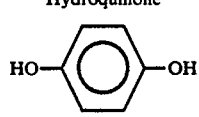

Benzoquinone

Isonox 129 - 2,2'-ethylidenebis[4,6-di-tert-butyl phenol]

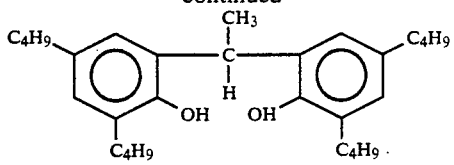

Ionol ® - 2,6-di-tert-butyl-4-methyl phenol

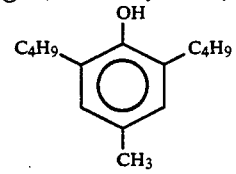

wt—weight
ppm—parts by weight per million parts by weight
microequiv. or microeq.—microequivalents
weight %—percentage by weight
ctsks—centistokes (viscosity at 25° C.)
hr.—hour
g.—gram or grams
cc—cubic centimeter

EXAMPLE 1

A 70 cc glass test cell, provided with a thermocouple and a Teflon TM coated magnetic stirring device, was charged, in a series of respective tests, with 50 gram samples of uninhibited 3-methacryloxypropyltrimethoxysilane (MAOP-TMS) and various inhibitors, after which the test cell was sealed air tight. The contents of the cell were then deoxygenated by sparging with dry nitrogen through an inlet and outlet connection at 200 cc/minute for 30 minutes to less than 0.5 ppm oxygen, sealed, and subjected to 140°±0.5° C. with continuous agitation. The time required for the material to gel was recorded in each test. The particular inhibitor employed and the amount thereof, expressed in ppm and microequivalents, as well as the results, are given in Table I which follows.

TABLE I

| Test | Inhibitor | ppm | Microeq. | Gellation Time (hr.) |
|---|---|---|---|---|
| A. | I | 200 | 38 | None noted after 7.5 days |
| B. | I | 10 | 1.9 | 77 |
| C. | MEHQ | 1000 | 403 | 10 |
| D. | Phenothiazine | 300 | 75.3 | 5.4 |
| E. | N,N'-diphenyl-p-phenylenediamine | 393 | 151.0 | 13.2 |

The data of Table I demonstrate the ability of Inhibitor I in the absence of molecular oxygen to inhibit polymerization of MAOP-TMS far more effectively than the inhibitors used in Tests C, D and E. In Test A, polymerization was inhibited for more than a week and in Test B for more than 3 days, whereas with the other inhibitors gelling occurred in less than a day. Even at the extremely low level of 10 ppm as in Test B, Inhibitor I was more effective than phenolic inhibitor MEHQ, phenothiazine and the aromatic diamine which were used in amounts of 1000, 300 and 393 ppm, respectively. The efficacy of Inhibitor I in inhibiting polymerization of MAOP-TMS is most dramatically demonstrated when compared on the basis of microequivalents (38 and 1.9 in Tests A and B versus 403, 75.3 and 151.0 of the respective inhibitors used in Tests C, D and E).

EXAMPLE 2

A 50 gram sample of uninhibited MAOP-TMS was charged to a vessel, MEHQ was added thereto, and the contents were then aerated and heated to 140°±0.5° C. without agitation. The time required for gellation to occur was recorded (Test A). The procedure was repeated using MEHQ in combination with Inhibitor I (Test B). The total number of microequivalents used in Test B was the same as in Test A (i.e., 54), the only difference between the two tests being that in Test B, 10 microequivalents of the MEHQ were replaced with 10 microequivalents of Inhibitor I. The results are:

| Test | Inhibitor | ppm | Microeq. | Gellation Time (hr.) |
|---|---|---|---|---|
| A. | MEHQ | 135 | 54 | 10 |
| B. | MEHQ/I | 110/53 | 44/10 | 30 |

As is apparent from this Example, the inhibitor combination was far more effective in preventing polymerization than MEHQ alone. This Example demonstrates that Inhibitor I is effective in preventing polymerization of MAOP-TMS when Inhibitor I is used in combination with other types of inhibitors. In addition, the much longer gellation time achieved in Test B also demonstrates the efficacy of Inhibitor I in the presence of oxygen.

EXAMPLE 3

The tests of this Example involved high vacuum (2 mm. Hg) batch distillation of crude 3-methacryloxypropyltrimethoxysilane using a standard laboratory glassware still system. The stability of pot contents was noted in each test. In one test, Inhibitor I was added to the silane prior to the distillation. In a second test, Ionol ® was used as the inhibitor. The results are:

| Test | Inhibitor | Weight % (ppm) | Microeq./ gram | Comments |
|---|---|---|---|---|
| A. | Ionol ® | 0.2 (2000) | 9.1 | Pot contents gelled in less than 1.5 hours during the heat up period and before the head temperature reached the boiling point of the product (100° C.). |
| B. | I | 0.1 (1000) | 3.8 | No gellation noted even at pot temperature in excess of 180° for two hours. |

The inhibitor level used in this Example is reported in microequivalents/gram of product because the distillation was done with different amounts of MAOP-TMS in the two tests. Inhibitor I successfully prevented polymerization of MAOP-TMS at distillation temperatures well in excess of its boiling point. The other sample of MAOP-TMS, inhibited with more than twice the level of Ionol on a microequivalent basis, polymerized during heatup. This Example demonstrates the ability of Inhibitor I to inhibit MAOP-TMS polymerization better than another phenolic inhibitor well known to this art.

EXAMPLE 4

A 250 cc three-necked round bottom flask was fitted with an addition funnel, Friedrich's condenser and thermometer. The flask was nitrogen purged and charged with 78.8 grams of distilled allyl methacrylate, 10 ppm Pt (as a solution of chloroplatinic acid) and heated to 95° C. The contents of the flask were continuously stirred by a magnetic stirrer. Distilled trimethoxysilane was slowly added to the flask and maintained at about 110° C. during the addition. The reaction mixture gelled before the entire addition (77.9 g) of trimethoxysilane was complete.

A second run was made with the addition of 0.394 gms (2514 ppm) of Inhibitor I to the allyl methacrylate prior to reaction. The trimethoxysilane addition was completed without gellation, yielding 76.1% crude 3-methacryloxypropyltrimethoxysilane, with a viscosity of 2.35 ctsks. The low viscosity of the resulting product further demonstrates that Inhibitor I prevented undesired polymerization during the hydrosilation reaction.

EXAMPLE 5

Respective 50 gram samples of uninhibited 3-acryloxypropyltrimethoxysilane were charged with various inhibitors, deoxygenated using the procedure described in Example 1, sealed and subjected to 140°±0.5° C. with continuous agitation. The time required for the material to gel was recorded in each test.

| Test | Inhibitor | ppm | Microeq. | Gellation Time (hr.) |
|---|---|---|---|---|
| A. | MEHQ | 25 | 10 | 17 |
| B. | Ionol ® | 44 | 10 | 73.5 |
| C. | I | 53 | 10 | 333 |

This Example again demonstrates the effectiveness of Inhibitor I to inhibit polymerization of acryloxysilanes in the absence of oxygen. Although the above inhibitors were all tested at the same microequivalents level, Inhibitor I prevented gellation for almost two weeks, while MEHQ prevented gellation for less than a day (Test A), and Ionol ® inhibited polymerization for slightly more than three days (Test B).

EXAMPLE 6

A 60.0 gram sample of crude, undistilled, 3-methacryloxypropyltrichlorosilane was deoxygenated using the procedure described in Example 1 and then subjected to 140° C. with continuous agitation. Gellation occurred in 0.5 hour.

The test was repeated except that a solution of 500 ppm of Inhibitor I in toluene was injected into the 3-methacryloxypropyltrichlorosilane at the onset of polymerization. The material was completely gelled in one hour.

This Example demonstrates that Inhibitor I was effective in prolonging gellation time at the relatively high temperature of 140° C. after polymerization had begun, and thus did function to some extent to slow down the rate of the polymerization. Nonetheless, the efficacy of Inhibitor I is most pronounced when provided to the (meth)acryloxysilane-containing medium to be stabilized, prior to the onset of polymerization.

EXAMPLE 7

As described in Example 1, Test B, a 50 gram sample of uninhibited 3-methacryloxypropyltrimethoxysilane was charged with 10 ppm (1.9 microequivalents) of Inhibitor I, deoxygenated, sealed and subjected to 140.0°±0.5° C. with continuous agitation. Gellation did not occur until 77 hours later, thereby demonstrating as previously noted the excellent performance of Inhibitor I in the absence of oxygen.

A second 50 gram sample was inhibited with 10 ppm of Inhibitor I, saturated with dry air (21 percent by volume oxygen), sealed and subjected to 140° C.±0.5° C. with continuous agitation. Gellation occurred immediately upon reaching 140° C. This Example demonstrates that an otherwise effective level of Inhibitor I (10 ppm) may not be sufficient to prevent polymerization of (meth)acryloxysilanes under a severe combination of conditions conducive to free radical formation. In such instances, the inhibitor must be provided in an amount sufficient to counteract free radical initiated polymerization such as 100 ppm or more.

EXAMPLE 8

Respective 50 gram samples of uninhibited 3-methacryloxypropyltrimethoxysilane were charged with various inhibitors, deoxygenated using the procedure described in Example 1, sealed and subjected to 140°±0.5° C. with continuous agitation. The time required for the material to gel was recorded in each test. The inhibitors employed and the results are given in Table II.

TABLE II

| Test | Inhibitor | Molecular Weight | ppm | Microequiv. | Gellation Time (hr.) |
|---|---|---|---|---|---|
| A | I | 263 | 24 | 4.57 | 49.6 |
| B | Hydroquinone/benzoquinone* | 109 | 5 | 4.57 | 6.5 |
| C | Isonox 129 | 438 | 19.9 | 4.54 | 2.5 |
| D | I | 263 | 12 | 2.28 | 17.8 |
| E | Hydroquinone/benzoquinone* | 109 | 12 | 10.9 | 24.0 |
| F | I | 263 | 5 | 0.95 | 2.8 |

*Based on total combined inhibitor; each component is equimolar.

This Example demonstrates the surprising ability of the Inhibitor I molecule to inhibit polymerization. In Tests A and B, the same number of equivalents were used. The ability of Inhibitor I to stabilize MAOP-TMS better than the hydroquinone/benzoquinone inhibitor combination is apparent by the dramatically longer gel time results (49.6 vs. 6.5 hrs). When Inhibitor I is compared to Isonox 129 (Test C), the improvement is even more apparent (49.6 vs. 2.5 hrs.).

Comparison of the hydroquinone/benzoquinone mixture (HQ/BQ) and Inhibitor I on an equal weight basis (Tests D and E) indicates that the HQ/BQ inhibitor combination prevented polymerization for a longer period of time than Inhibitor I. This result is explained by the lower molecular weight and dual functionality of the hydroquinone and benzoquinone compounds, resulting in a higher number of equivalents than Inhibitor I when an equal weight of the compounds is used; refer to Table A. Inhibitor I, when used at only approximately one-fifth the microequivalents of the HQ/BQ inhibitor combination (2.28 vs. 10.9), inhibited polymerization for almost three-quarters of the gel time achieved with the hydroquinone/benzoquinone combination (17.8 v. 24 hours).

Finally, even at the extremely low level of 5 ppm., Inhibitor I outperformed other tertiary-butyl substituted phenolic inhibitors known to the art. Thus in Test F, Inhibitor I was used at only approximately 25% the level of Isonox 129 used in Test C (5 vs. 19.9 ppm) and still outperformed the other phenolic inhibitor.

EXAMPLE 9

Respective samples of 3-methacryloxypropyltrimethoxysilane were stabilized with various levels of the hydroquinone/benzoquinone (HQ/BQ) inhibitor combination and with Inhibitor I. The color of the samples was tested with the following results.

| HQ/BQ TOTAL CONCENTRATION (ppm) | Color | INHIBITOR I CONCENTRATION (ppm) | Color |
|---|---|---|---|
| 0 | 10-20 PtCo | 0 | 10-20 PtCo |
| 9.5 | 30 PtCo | 245.6 | 10-20 PtCo |
| 41.6 | 40 PtCo | 587.6 | 10-20 PtCo |
| 82.4 | 80 PtCo | | |
| 487.5 | <1 GVS | | |
| 982.8 | 1-2 GVS | | |
| 1944.2 | 2 GVS | | |

The color results are reported in platinum-cobalt (PtCo) units or Gardner Varnish Stain (GVS) units. Both tests are used to measure the color of the sample with low numbers representing desired values. The PtCo test is a much more sensitive test than the Gardner Varnish Stain method. Consequently, the PtCo test is employed until a reading exceeding the maximum value (100 PtCo units) is registered; thereafter the GVS method is employed.

Control samples (no inhibitor added) were included in the tests to obtain baseline values. The samples with platinum-cobalt colors of 10-20 units are essentially colorless. When the level of HQ/BQ was raised to approximately 10 ppm, the color of the sample appreciably changed. With increasing levels of HQ/BQ, the color of the MAOP-TMS sample became increasingly poorer until the platinum-cobalt test was no longer appropriate to measure the sample's color. Thus, at 487.5 ppm of HQ/BQ, the color of the sample had become so poor that the platinum-cobalt test was no longer appropriate and the less sensitive Gardner Varnish Stain test was employed.

In marked contrast, the sample containing 587.6 ppm of Inhibitor I had a color equivalent to the control sample containing no inhibitor. The non-chromophoric nature of Inhibitor I allows this inhibitor to be employed even at high levels (e.g., 587 ppm) without adversely affecting product color.

EXAMPLE 10

A 500 cc round bottom, four-necked flask fitted with a water condenser, thermometer, addition funnel, magnetic stirrer and nitrogen inlet was charged with 139 grams (1.10 moles) of allylmethacrylate to which was added 10 ppm of Inhibitor I. The contents of the flask were heated to 70° C. and then charged with 5 cc of trichlorosilane and a chloroplatinic acid solution (18.8 ppm Pt based on the allylmethacrylate charge) to initiate the reaction. A second slow, continuous addition of 133.5 grams (0.986 mole) of trichlorosilane was made while maintaining the reaction temperature at 65°–70° C. Gas chromatographic analysis indicated complete reaction of the trichlorosilane and a resulting product of 3-methacryloxypropyltrichlorosilane (86% purity). The product was inhibited with an additional 17 ppm of Inhibitor I, and a 60 gram sample was heated to 140° C. under anaerobic conditions with continuous agitation. The sample did not gel after maintaining these conditions for over 45 hours.

The above Example demonstrates the effectiveness of Inhibitor I at low levels in preventing polymerization during the silane-forming hydrosilation reaction and purification of the silylated product.

EXAMPLE 11

A 204.2 gram sample of MAOP-TMS was inhibited with 93 ppm of Inhibitor I and charged to a 250 cc flask. The contents of the flask were continuously stirred and distilled at 5 mm Hg at a pot temperature of 130°–150° C. The total distillation time was 3.0 hours. A total of 194.9 grams of distillate was recovered. Chromatographic analysis revealed 99.6% product purity in the distillate.

The above Example demonstrates the ability of Inhibitor I at low levels (i.e. less than 100 ppm) to prevent polymerization of MAPO-TMS during its purification by distillation over an extended period of time.

We claim:

1. A stable composition comprising an acryloxysilane or a methacryloxysilane and an N,N-dialkylaminomethylene phenol in an amount at least sufficient to prevent polymerization of the silane.

2. The composition of claim 1 wherein the phenol is a 2,6-dialkyl-4-N,N-dialkylaminomethylene phenol.

3. The composition of claim 1 wherein the phenol is 2,6-di-tert-butyl-4-dimethylaminomethylene phenol.

4. The composition of claim 1 wherein the silane has the formula, $CH_2=C(R)C(O)-O-R''-SiY_3$, where R is hydrogen or methyl, R'' is alkylene of one to four carbon atoms and Y is halide or an alkoxy group of one to four carbon atoms.

5. The composition of claim 4 wherein the silane is 3-methacryloxypropyltrimethoxysilane.

6. The composition of claim 1 which is substantially free of molecular oxygen.

7. The composition of claim 1 wherein the N,N-dialkylaminomethylene phenol is present in an amount up to about 500 ppm, based on the weight of the silane.

8. The composition of claim 1 in which the silane is 3-methacryloxypropyltrimethoxysilane and the phenol is 2,6-di-tert-butyl-4-dimethylaminomethylene phenol present in an amount from 5 to 200 ppm, based on the weight of the silane.

9. The composition of claim 1 which additionally contains at least one other polymerization inhibitor different from said N,N-dialkylaminomethylene phenol.

10. The composition of claim 9 wherein said other inhibitor contains phenolic, amino or quinone functionality or a combination thereof.

11. The process of producing acryloxysilanes or methacryloxysilanes which comprises providing to an acryloxysilane- or methacryloxysilane-forming reaction mixture an N,N-dialkylaminomethylene phenol in an amount at least sufficient to prevent polymerization of the silane product.

12. The process of claim 11 wherein the phenol is a 2,6-dialkyl-4-N,N-dialkylaminomethylene phenol.

13. The process of claim 11 wherein the reaction mixture contains allyl methacrylate and a trialkoxysilane, and the silane product is a 3-methacryloxypropyltrialkoxysilane.

14. The process of claim 11 wherein the reaction mixture contains allyl methacrylate and trichlorosilane, and the silane product is 3-methacryloxypropyltrichlorosilane.

15. The process of distilling acryloxysilanes or methacryloxysilanes from a mixture containing same which comprises providing to said mixture an N,N-dialkylaminomethylene phenol in an amount at least sufficient to prevent polymerization of said acryloxysilane or methacryloxysilane during said distillation.

16. The process of claim 15 wherein said distillation is conducted at subatmospheric pressure.

17. The process of claim 16 wherein the phenol is a 2,6-dialkyl-4-N,N-dialkylaminomethylene phenol.

18. The process of claim 16 wherein the silane undergoing distillation has the general formula, $CH_2=C(R)C(O)-O-R''-SiY_3$, where: R is hydrogen or methyl; R'' is alkylene of one to four carbon atoms; and Y is halide or an alkoxy group of one to four carbon atoms.

19. The process of claim 18 wherein said silane is 3-methacryloxypropyltrimethoxysilane.

20. The process of claim 19 wherein the phenol is 2,6-di-tert-butyl-4-dimethylaminomethylene phenol.

21. In a process for producing acryloxysilanes or methacryloxysilanes, the improvement which comprises providing to an acryloxy- or methacryloxysilane-forming reaction an N,N-dialkylaminomethylene phenol in an amount at least sufficient to prevent polymerization of the reaction mixture, subjecting the reaction mixture to distillation in the presence of an N,N-dialkylaminomethylene phenol in an amount at least sufficient to prevent polymerization during distillation, and providing an N,N-dialkylaminomethylene phenol to the distillate in an amount at least sufficient to inhibit polymerization of the acryloxysilane or methacryloxysilane product contained therein.

22. The process of claim 21 wherein the acryloxy- or methacryloxysilane-forming reaction comprises a hydrosilation reaction, and the N,N-dialkylaminomethylene group of said phenol is positioned para to the phenolic hydroxyl group.

23. The process of claim 22 wherein allyl methacrylate and trimethoxysilane are reacted in the hydrosilation reaction and the product is 3-methacryloxypropyltrimethoxysilane.

24. The process of claim 22 wherein allyl methacrylate and trichlorosilane are reacted in the hydrosilation reaction to provide a reaction mixture containing 3-methacryloxypropyltrichlorosilane, and the 3-methacryloxypropyltrichlorosilane is reacted with an alcohol in the presence of said N,N-dialkylaminomethylene phenol to produce the corresponding 3-methacryloxypropyltrialkoxysilane which is provided to the distillation step.

25. The process of claim 21 wherein the N,N-dialkylaminomethylene phenol is 2,6-di-tert-butyl-4-dimethylaminomethylene phenol.

* * * * *